United States Patent
Vojtisek-Lom

(12) 
(10) Patent No.: US 6,308,130 B1
(45) Date of Patent: Oct. 23, 2001

(54) PORTABLE ON-BOARD MASS EMISSIONS MEASURING SYSTEM

(75) Inventor: Michal Vojtisek-Lom, Pittsburgh, PA (US)

(73) Assignee: Clean Air Technologies International, Inc., Clarence Center, NY (US)

(*) Notice: Subject to any disclaimer, the term of this patent is extended or adjusted under 35 U.S.C. 154(b) by 0 days.

(21) Appl. No.: 09/359,984

(22) Filed: Jul. 23, 1999

(51) Int. Cl.[7] ............. G01M 15/00; G01N 1/22; G06F 15/04
(52) U.S. Cl. ............. 701/114; 73/23.31; 73/118.1
(58) Field of Search ............. 73/23.31, 23.32, 73/23.33, 1.06, 116, 117.2, 117.3, 118.1, 863.03, 863.01, 863.81; 701/114; 702/182, 187

(56) References Cited

U.S. PATENT DOCUMENTS

| | | | |
|---|---|---|---|
| 5,099,437 | * 3/1992 | Weber | 702/187 |
| 6,062,092 | * 5/2000 | Weaver | 73/863.03 |
| 6,148,656 | * 11/2000 | Breton | 73/23.31 |
| 6,151,952 | * 11/2000 | Mathews et al. | 73/23.31 |

OTHER PUBLICATIONS

Michal Vojtisek–Lom and James T. Cobb, Jr., Vehicle Mass Emissions Measurement Using Portable 5–gas Exhaust Analyzer and Engine Computer Data, presented at Emission Inventory: Planning for the Future Conference, Research Triangle Park, North Carolina, Oct. 28–30, 1997.

Michal Vojtisek–Lom and James T. Cobb, Jr., On–road Light–duty Vehicle Emission Measurements Using a Novel Inexpensive On–board Portable System; presented at the Eighth CRC On–road Vehicle Emissions Workshop, San Diego, California, Apr. 20–22, 1998.

Michal Vojtisek–Lom and James T. Cobb, Jr., Measurement, Variance and Reduction of Real–world Emissions of 20 Dedicated CNG Vans; presented at Air & Waste Management Association Annual Meeting, San Diego, California, Jun. 14–18, 1998.

\* cited by examiner

*Primary Examiner*—Willis R. Wolfe
(74) *Attorney, Agent, or Firm*—Phillips, Lytle, Hitchcock, Blaine & Huber LLP

(57) ABSTRACT

The invention is directed to an improved portable on-board mass emissions measuring system for internal combustion engines. In the preferred embodiment, the system is comprised of an exhaust analyzer (16), at least one sensor (18, 22 or 29) which may be temporarily attached to the engine for sensing parameters of the engine, and a processor (19) programmed to collect and manipulate data from the analyzer and the sensor, whereby the mass emissions of the engine may be calculated. The system may further comprise a display (20) for displaying the mass emissions of the engine and an engine-control interface (21). The sensor may be capable of sensing engine RPM, engine oil temperature, or intake manifold pressure. The exhaust analyzer may be capable of measuring concentrations of the engine exhaust constituents, particulates, aerosols, and gases in the engine emissions. The present invention also discloses a portable mass emissions measuring system for an internal combustion engine comprising an exhaust analyzer (16), a trace-gas injector (23), and a processor (19) programmed to collect and manipulate data from the analyzer and the injector, whereby the mass emissions of the engine may be calculated. In addition, the present invention is directed to a method for determining the emission flow rate of an internal combustion engine with the trace-gas injector.

20 Claims, 7 Drawing Sheets

PORTABLE ON-BOARD MASS EMISSIONS MEASURING SYSTEM

FIELD OF THE INVENTION

The present invention relates generally to the field of vehicle emissions measuring systems and, more particularly, to an improved on-board mass emissions measuring system.

BACKGROUND ART

Motor vehicle emissions are the leading source of air pollution in most metropolitan areas, causing health, ecological and economical damage. As a result, considerable effort and resources are currently devoted to various emission reduction strategies, such as emission inspection programs, reformulated or alternative fuels, stricter standards for new vehicles, mass transit, improved engine control and catalyst technologies, and upgrade and repair of existing vehicles. However, in order to evaluate the impact of these reduction strategies, it is necessary to measure and collect accurate real-world emission measurements over the life of a vehicle.

Presently, the vast majority of emission tests are performed in a specialized laboratory, where the vehicle is driven on a dynamo meter according to a prescribed driving cycle, such as I/M 240 or FTP for light and medium duty vehicles and CBD for heavy duty vehicles.

This approach has several significant disadvantages: (1) the driving cycles do not adequately represent real-world driving conditions, which vary and are often unknown; (2) vehicles can be optimized for low emissions during the driving cycle, but do not operate optimally in actual use; (3) the testing equipment is bulky and expensive; (4) there are significant costs associated with testing the vehicle, such as vehicle (and/or mobile laboratory) mileage, vehicle downtime, and the test itself, especially on heavy-duty vehicles; (5) individual vehicles engines have unique characteristics which effect emissions, and (6) only a relatively small number of vehicles can be tested.

The first two disadvantages can be eliminated by using a testing system mounted on the vehicle. However, the use of an on-board system is presently limited to repair grade gas analyzers that provide only a rough estimate of mass emissions for repair purposes and a relatively small number of dedicated instrumented vehicles.

For example, it is known that an on-board testing system mounted on a dedicated instrumented vehicle was disclosed by Sierra Research. This system uses a repair-grade four-gas non-dispersive infra-red (NDIR) analyzer to measure exhaust gas concentrations and several sensors mounted on the engine to determine intake air flow. From these measurements, exhaust mass flow and mass emissions can be computed.

A simpler system, using repair grade NDIR analyzer concentration data only, has been developed at the University of Denver to predict I/M 240 mass emissions. Using this system, the average ratio of pollutant to fuel consumed is calculated from the concentration data. The amount of fuel consumed is then estimated from the length of the trip and fuel economy. While this method is successful in predicting whether a vehicle will pass or fail an I/M 240 test, and has been incorporated into newer repair grade analyzers, it is not sufficiently accurate in measuring actual mass emissions, since it does not properly account for emissions during extreme (high or low) exhaust flow. Also, errors in estimating fuel consumption results in the same relative error in mass emission readings.

Accordingly, a system which allows for the testing of individual vehicles during daily operation is necessary to eliminate many of the shortfalls found in the existing systems. One such system was previously disclosed by the inventor. The system employs a five-gas analyzer drawing undiluted exhaust from the tailpipe and calculates mass exhaust flow from engine operating data obtained via a diagnostic link to the computer controlled engine. However, this system can only be employed on engines which include a computerized engine control unit. This greatly limits the number and type of vehicles from which emission measurements may be taken.

Hence, it would be useful to provide a portable mass emissions measuring system which could measure accurate real-world vehicle emissions on a large variety of vehicles without displacing the vehicle from service.

DISCLOSURE OF THE INVENTION

With parenthetical reference to the corresponding parts, portions or surfaces of the disclosed embodiment, merely for the purposes of illustration and not by way of limitation, the present invention provides an improved mass emissions measuring system (15) for an internal combustion engine (17), comprising an exhaust analyzer (16), at least one sensor (18, 22 or 29) which may be temporarily attached to the engine for sensing parameters of the engine, and a processor (19) programmed to collect and manipulate data from the analyzer and the sensor, whereby the mass emissions of the engine may be calculated.

The system may further comprise a display (20) for displaying the mass emissions of the engine. The system may also include an engine-control interface (21). The sensor may be capable of sensing engine RPM, engine oil temperature, or intake manifold pressure. The exhaust analyzer may be capable of measuring concentrations of the engine exhaust constituents, particulates, aerosols, and gases in the engine emissions. The system may be adapted for use on-board a moving vehicle. The present invention also discloses a portable mass emissions measuring system for an internal combustion engine comprising an exhaust analyzer (16), a trace-gas injector (23), and a processor (19) programmed to collect and manipulate data from the analyzer and the injector, whereby the mass emissions of the engine may be calculated.

The present invention also discloses a method for determining the emission flow rate of an internal combustion engine, comprising the steps of providing an internal combustion engine having an exhaust, providing an exhaust analyzer having a sampling point downstream from the engine, operating the engine, injecting a trace-gas upstream from the sampling point of the exhaust analyzer at a controlled flow rate, measuring concentrations of the trace-gas with the exhaust analyzer, and calculating the emissions flow rate of the engine based on the known trace-gas injection flow rates and measured trace-gas concentrations.

Accordingly, the general object of the present invention is to provide an improved mass emissions measuring system which is adapted to be used to determine real-world vehicle emissions.

Another object is to provide an improved system for determining vehicle emissions which is portable.

Another object is to provide an improved system which is adapted for use on a wide variety of vehicles.

Another object is to provide an improved system which may be used on a vehicle without permanent modification to the vehicle Another object is to provide an improved emission measuring system which can be installed for use in a vehicle in a very short period of time.

Another object is to provide an improved mass emissions measuring system which may be used without displacing a vehicle from service.

Another object is to provide an improved emissions measuring system which allows for use with a large number of vehicles.

Another object is to provide an improved emissions measuring system which may be used on vehicles which do not have an engine electronic control unit.

DESCRIPTION OF THE PREFERRED EMBODIMENTS

Figure 1:
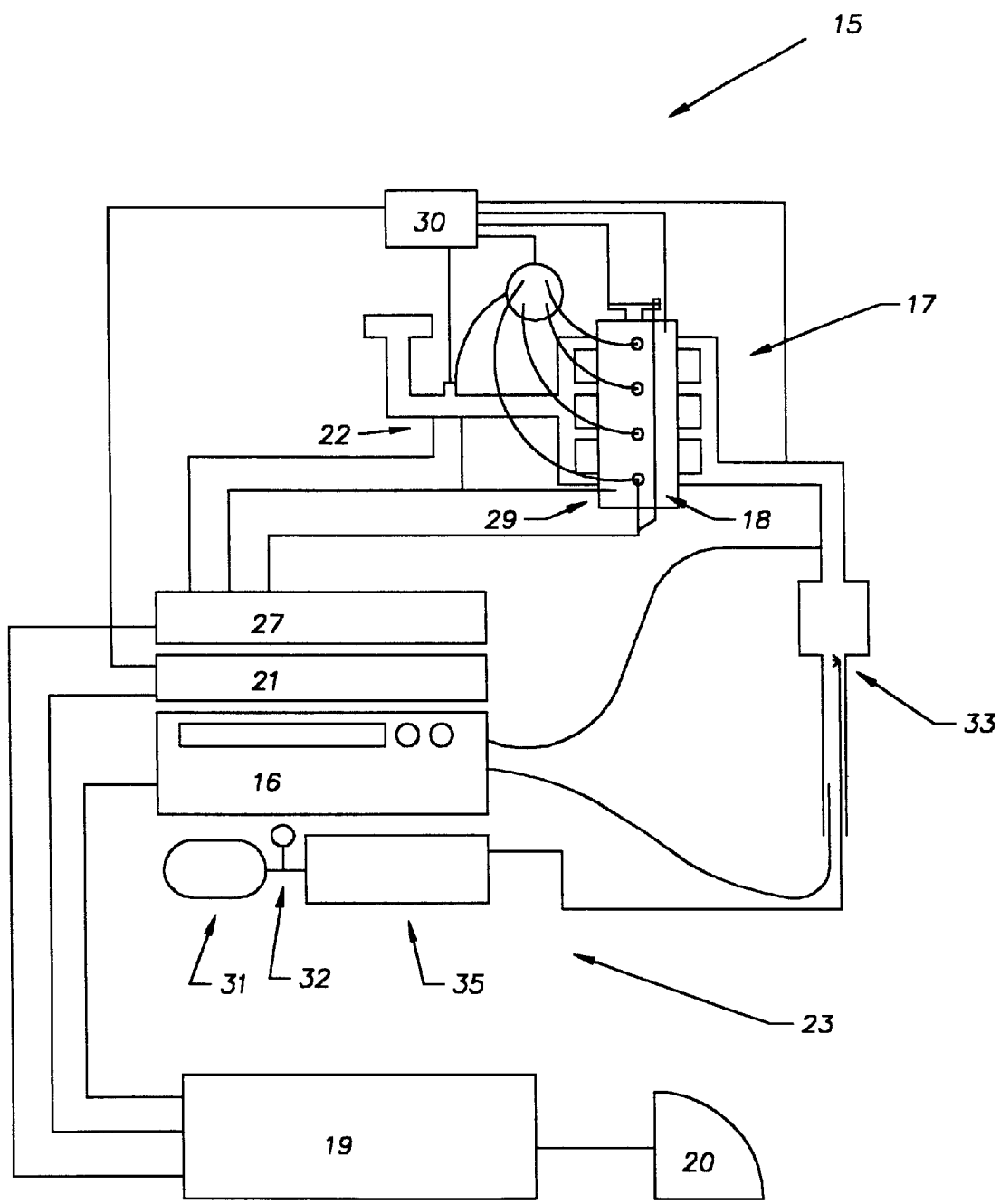
FIG. 1 is a complete schematic of the emissions measuring system.

At the outset, it should be clearly understood that like reference numerals are intended to identify the same structural elements, portions or surfaces consistently throughout the several drawing figures, as such elements, portions or surfaces may be further described or explained by the entire written specification, of which this detailed description is an integral part. Unless otherwise indicated, the drawings are intended to be read (e.g., cross-hatching, arrangement of parts, proportion, debris, etc.) together with the specification, and are to be considered a portion of the entire written description of this invention. As used in the following description, the terms "horizontal", "vertical", "left", "right", "up" and "down", as well as adjectival and adverbial derivatives thereof, (e.g., "horizontally", "rightwardly", "upwardly", etc.), simply refer to the orientation of the illustrated structure as the particular drawing figure faces the reader. Similarly, the terms "inwardly" and "outwardly" generally refer to the orientation of a surface relative to its axis of elongation, or access of rotation, as appropriate.

Referring now to the drawings, and, more particularly, to FIG. 1 thereof, this invention provides an improved portable mass emissions measuring system, of which the presently preferred embodiment is generally indicated at 15. The system is shown as broadly including an exhaust analyzer 16, three engine sensors 18, 22, and 29, a sensor data acquisition interface 27, an engine control interface 21, and a processor 19.

Figure 2:
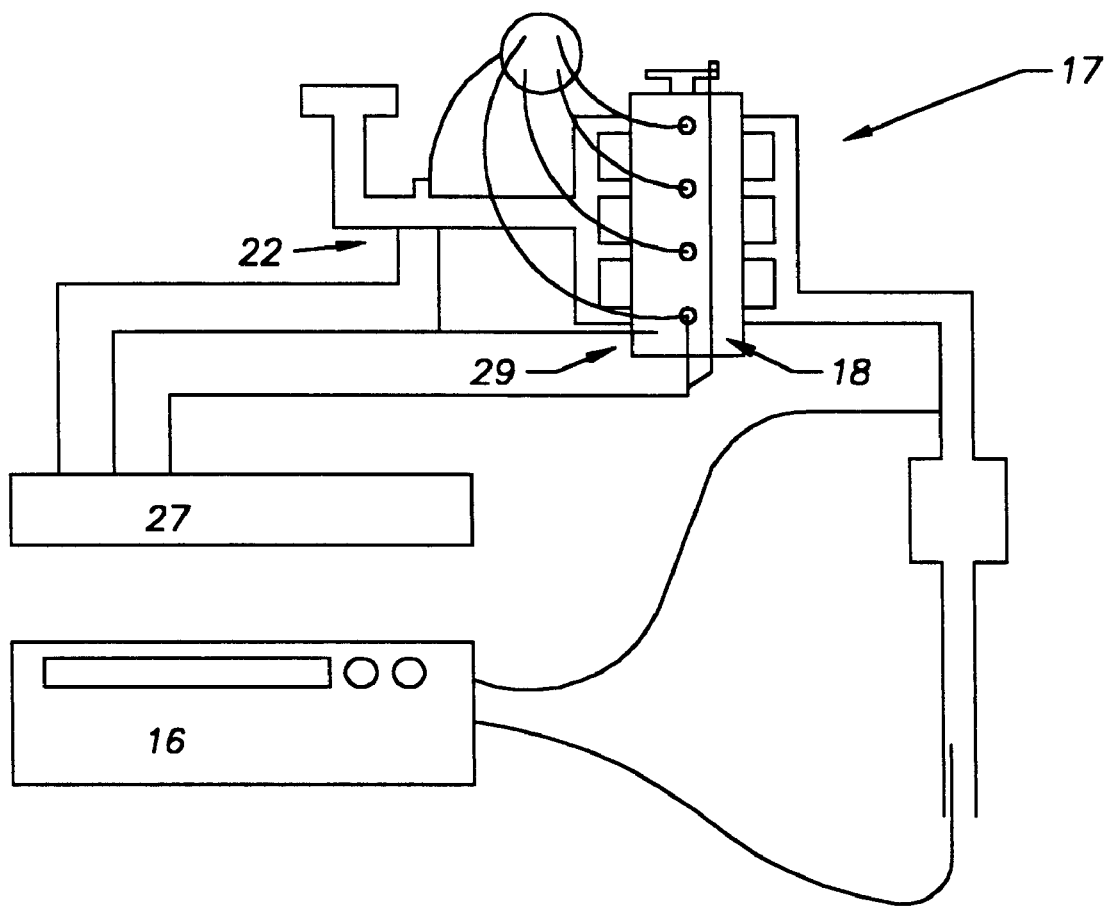
FIG. 2 is a partial schematic of the emissions measuring system showing the sensors temporarily mounted to the engine.

As shown in FIG. 2, in engines which are not computer controlled, engine rpm, intake manifold pressure and intake oil temperature are measured using engine rpm sensor 18, intake manifold pressure sensor 22, and intake oil temperature sensor 29. Sensors 18, 22, and 29 are adapted to be temporarily mounted to the engine during testing. Data acquisition interface 27 is a conventional converter which converts analogue readings from the sensors to digital output.

Figure 3:
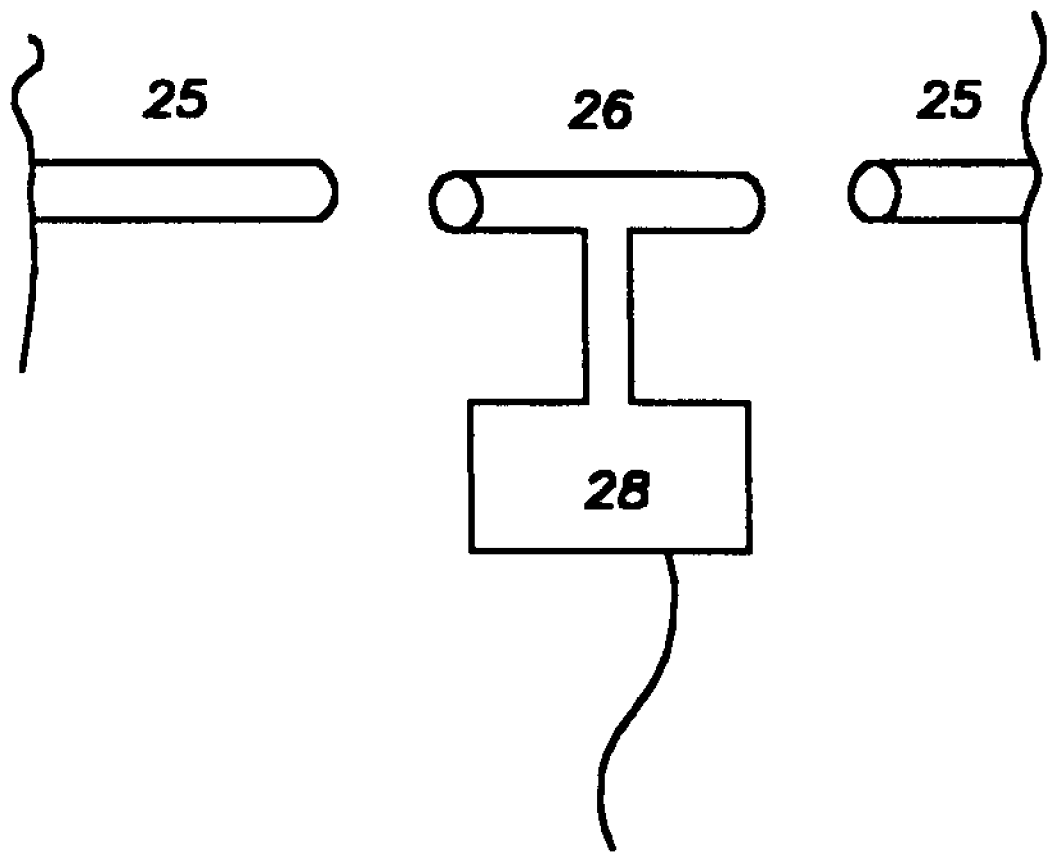
FIG. 3 is an exploded view of the manifold pressure sensor.

Oil temperature sensor 29 is a conventional dipstick temperature probe which is inserted in place of the oil dip-stick. Engine rpm sensor 18 is a standard rpm pickup probe, which is adapted to clamp onto one of the engine's spark-plug wires. The dipstick temperature probe and rpm inductive clamp manufactured by OTC, a division of SPX Corporation, of Owatonna, Minn. 55060-1171 may be employed in the preferred embodiment. As shown in FIG. 3, manifold pressure sensor 22 is a pressure sensor added to an existing engine vacuum line 25. In the preferred embodiment, pressure sensor 22 is adapted to take readings from the engine's timing advance line. As shown, a T-adaptor 26 is inserted in vacuum line 25 and connected to a pressure transducer 28. Pressure transducer 28 includes a link to processor 19 such that the manifold pressure or vacuum may be recorded and stored.

Figure 4:
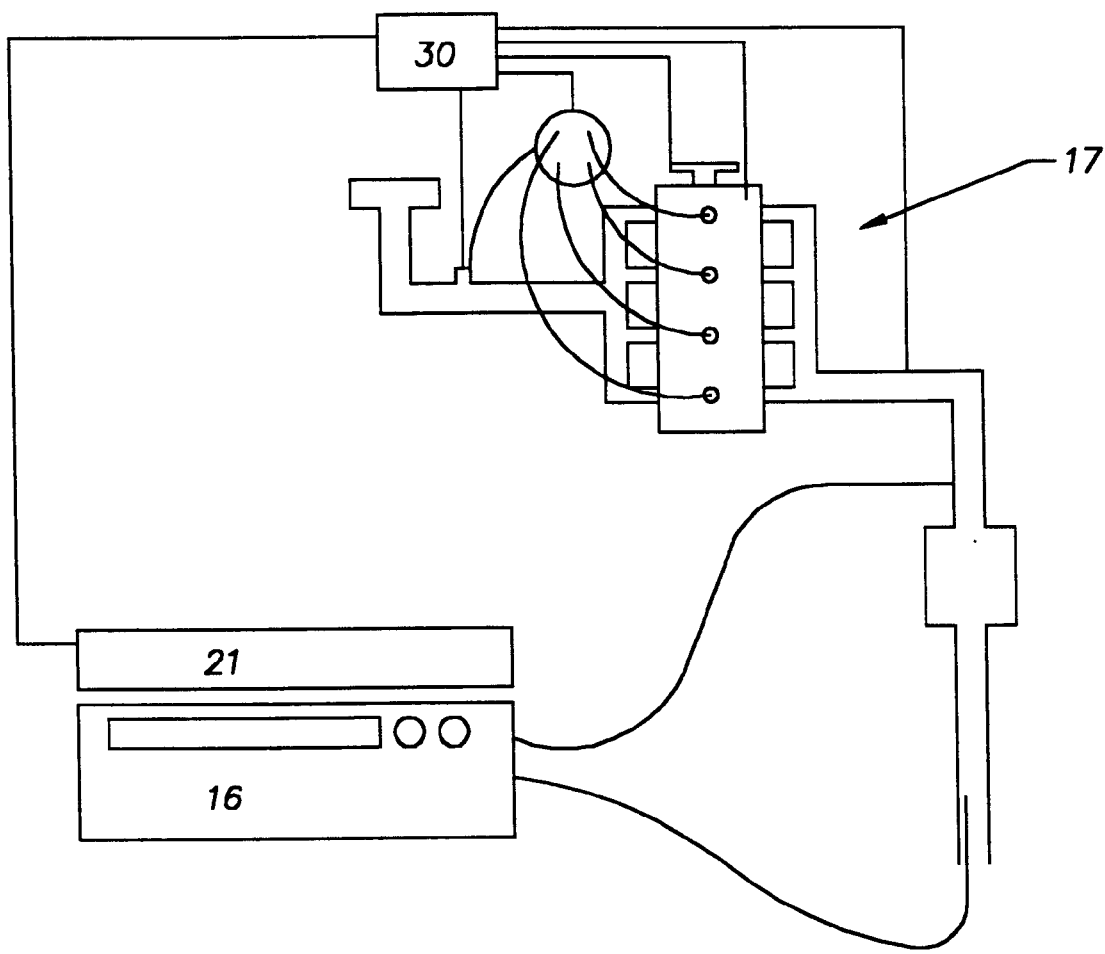
FIG. 4 is a partial schematic of the emissions measuring system showing the control unit interface.
Figure 5:
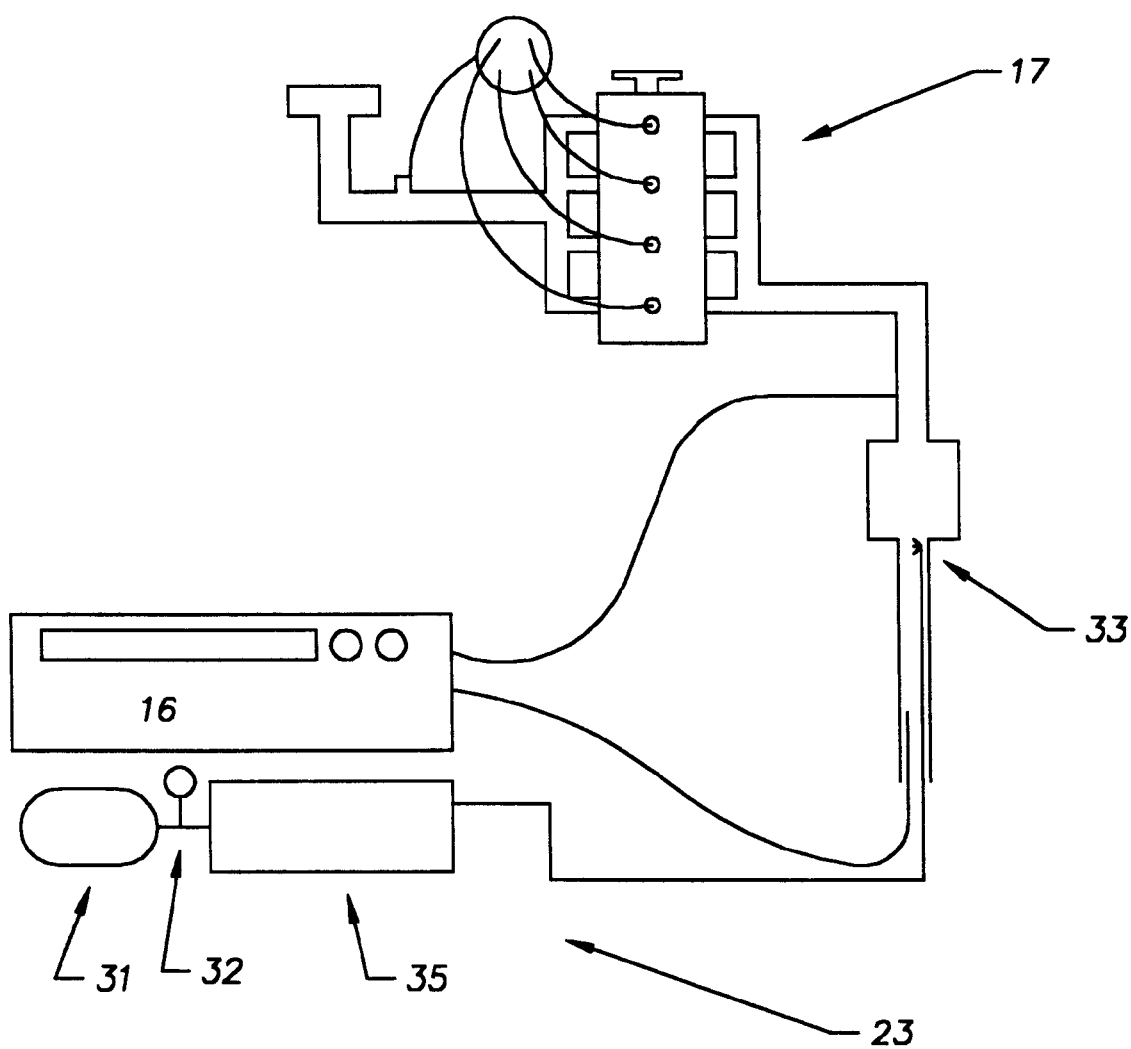
FIG. 5 is a partial schematic of the emissions measuring system showing the trace gas injector.

As shown in FIG. 4, on computer controlled engines where engine data can be obtained by an engine diagnostic link, intake air flow or fuel flow is computed from the engine data obtained by engine control interface 21. Because modern computer-controlled engines provide operating data such as vehicle speed, engine rpm, intake air and coolant temperature, intake air pressure, intake air mass flow, throttle position and engine load through an engine control unit 30, this information can be fed to processor 19 by engine control interface 21. The Snap-On MT-2500 engine diagnostic scanner manufactured by Snap-On Diagnostics of Kenosha, Wis. 53141-1410 may be employed in the preferred embodiment.

As explained in greater detail below, processor 19 is programmed to use data from engine control unit 30 to compute exhaust mass flow, which, when multiplied by the measured concentrations of pollutants in the exhaust gas, provides grams per second emissions data. Additional computations provide second-by-second and total grams per gallon and grams per mile emissions, and fuel consumption. Mass emissions in grams per second of a pollutant X for each second are obtained by multiplying concentration of X in the exhaust, measured by exhaust analyzer 16, by the mass flow of exhaust. By numerical integration of time and distance, grams per mile emissions are then obtained. Processor 19, exhaust analyzer 16, data acquisition interface 27 and engine control unit interface 21 are enclosed in a single aluminum housing 37 (not shown), which is vented for heat dispersion and adapted for placement in the seat of a vehicle.

Figure 6:
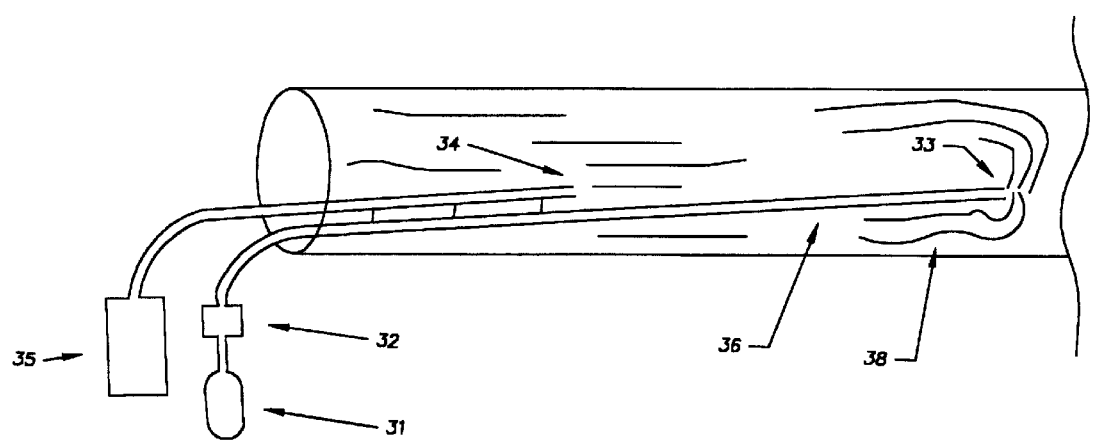
FIG. 6 is a schematic showing the trace gas injector.
Figure 7:
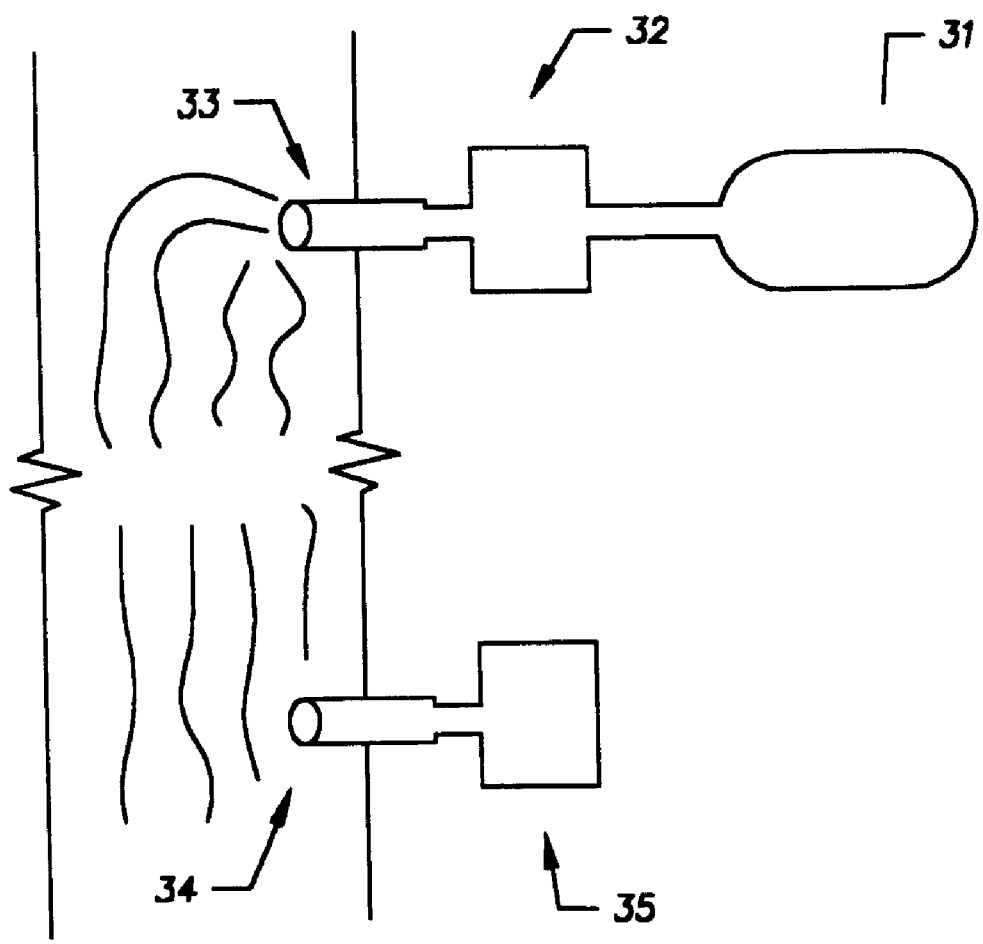
FIG. 7 is a schematic showing an alternate embodiment of the trace gas injector.

As an alternative to the use of sensors 18, 22, and 29, or engine control interface 21, a trace-gas injector 23 may be used to determine exhaust flow. As shown in FIGS. 6 and 7, exhaust flow can be measured by injecting a small known continuous flow of a non-reactive trace gas. As shown in FIG. 6, trace-gas injector 23 comprises an inert gas reservoir 31, a flow regulator 32, an injector 33, a downstream sampler 34 and an inert gas analyzer 35. Injector 33 is placed at an upstream location in the exhaust of a vehicle so as to obtain a homogenous mixture at the sampling point. Helium or neon may be used as the inert gas. The inert gas is fed from inert gas reservoir 31 through a flow-regulator 32 and injected into the exhaust stream. In the preferred embodiment, flow regulator 32 is calibrated so as to inject about 50 to 500 ccm of gas per minute so that the concentration of inert gas is about 1 to 50 ppm. Injector 33 disburses the gas at an upstream point in a fairly uniform manner into the exhaust stream. Sampler 34 is located downstream from injector 33. Sampler 34 takes a sample of the exhaust stream which is then transferred by an appropriate inert gas analyzer 35. Alternatively, exhaust analyzer 16 may be used to determine concentrations of the inert gas, rather than a separate sampler 34 and inert gas analyzer 35. Inert gas analyzer 35 and regulator 32 are also enclosed in housing 37.

The inert gas concentration Ic determined by gas analyzer 34 will equal the inert gas flow If divided by the sum of the exhaust gas flow Ef and inert gas flow If. The inert gas flow is a known quantity as regulated by flow regulator 32. Accordingly, the exhaust flow Ef is $$Ef = If\left(\frac{(1-Ic)}{Ic}\right)$$

To determine the concentration of pollutant such as hydrocarbons (HC), carbon monoxide (CO), nitrogen oxides ($NO_x$), carbon dioxide ($CO_2$) and Oxygen ($O_2$) in the exhaust of engine 17, exhaust gas is drawn from the tailpipe into gas analyzer 16, located in the vehicle. Raw, undiluted exhaust is collected through a 12" probe inserted into the tailpipe and secured by a hose clamp. The exhaust gas is then drawn at a rate of approximately 0.1 liters per second through a ¼" sampling hose, secured by clamps to a set of in-line filters. The in-line filters are located before the analyzer 16 inlet and remove virtually all water and particulate matter from the sample. The filters may include a pre-filter to remove large diesel exhaust particles, a coarse filter, and a fine 0.01 mm coalescing filter that removes heavy aerosols and most of the water vapor.

The gas is then pumped into exhaust analyzer 16. Exhaust analyzer 16 is a modified repair-grade five-gas non-dispersive infra-red (NDIR) exhaust analyzer, which provides near real-time readings of concentrations of HC, CO, $CO_2$, $NO_x$ and $O_2$. The analyzer is powered from a cigarette lighter adaptor or by a fused cable connected directly to the vehicle battery. The OTC RG-240 digital five-gas analyzer manufactured by OTC may be employed in the preferred embodiment.

On natural gas powered vehicles, and/or where methane and non-methane hydrocarbons (NMHC) are to be measured separately, several options exist. First, a hand-held methane/low-range CO NDIR analyzer is added to the system. From a known concentration of methane and a known (experimentally determined) response of the 5-gas analyzer to methane (ratio of detected to actual methane concentration), both methane and NMHC concentrations can be obtained. A second NDIR unit with different response to methane is added. The methane and NMHC concentrations are then obtained from the two different HC readings by each analyzer. A portable flame ionization detector (FID) is added to measure total hydrocarbons (THC); from the known response of the NDIR analyzer to methane, and HC and THC readings, both methane and NMHC emissions can be determined. All calculations are simple arithmetic.

To obtain mass emissions data, the sample to be analyzed must be drawn from a known flow of gas. Traditionally, dilution tunnels and constant volume samplers were used for this purpose. In the preferred embodiment, the system samples undiluted exhaust and measures the exhaust flow in real-time. To calculate exhaust flow, either intake mass air flow or fuel flow must be known. Also, vehicle speed is necessary for distance and real-time fuel economy (mpg) and emissions (grams/mile, grams/gallon) calculations. Additional data, such as engine temperature, throttle position, or air conditioning operation are useful in correlating emission data to particular driving operations.

As mentioned above, on most modern engines, intake air mass flow and/or fuel flow can be obtained from engine electronic controls using engine control interface 21 which is commercially available. On throttled (such as gasoline powered) engines, the intake air flow ($MF_i$) is usually determined by the formula:

$$MF_i\,[mol/s] = \left(\frac{\frac{(\text{Adjusted } MAP\,[\text{kPa}])(\text{Engine displacement [liters]})/}{(\text{engine speed [rpm]})}}{\frac{30\,(\text{engine cycle})}{8.314\,(\text{intake air temp. [deg. C.]} + 273)}}\right) VEF$$

MAP is the manifold absolute pressure and the engine cycle will be either 2 or 4. VEF is the volumetric efficiency of engine 17 at full throttle and $$\text{Adjusted } MAP = \text{Measured } MAP - \frac{\text{Atmospheric pressure}}{\text{Engine compression ratio}}$$

If the intake air temperature is not available, it is approximated by the arithmetic average of engine coolant or oil temperature and ambient air temperature. Some engines report intake air mass flow directly in grams per second.

On naturally aspirated diesel engines, atmospheric pressure is used instead of Measured MAP. On turbo-charged engines, Measured MAP can be substituted by a sum of the atmospheric pressure and turbo boost, where turbo boost is the difference between the intake manifold pressure and atmospheric pressure.

Fuel flow can be obtained either directly as a mass or volume per second (such as on some heavy-duty diesel engines), or calculated from a formula:

$$\text{FuelFlow} = (\text{Injector displacement})(\text{number of cylinders})\left(\frac{\text{Engine rpm}}{30\,(\text{engine cycles})}\right)$$

Injector displacement is the amount of fuel injected by one injector during one engine cycle. Injector displacement is directly proportional to the injector pulse width, reported by many non-diesel engines. The proportion constant may be obtained from the vehicle manufacturer or determined experimentally.

As shown in FIG. 1, sensors 18, 22 and 29, engine control interface and exhaust analyzer 16 are connected to a processor via a serial (RS-232) port. An Axiom P-1000 panel PC may be used in the preferred embodiment. The present system uses software written by the inventor to simultaneously receive both sets of data. Also, the user is allowed, at any time during the measurement, to enter a tag to mark sections of data as desired. The ASCII-text data is parsed, a system time stamp and the most recent tag is added to each complete record, and each record is stored in computer memory.

Processor 19 is programmed to synchronize the data received. Sensors 18, 22, 29 and exhaust analyzer 16 produce data with a certain delay (or response time), at a certain rate, and with gaps. Both the delay and the rate can be obtained from the instrument manufacturer and/or obtained experimentally. The gaps are caused by equipment malfunction or by events such as periodic zeroing of exhaust analyzer 16.

On each set of data, the delay is subtracted from the time stamp. Linear interpolation is then used to generate one record every second (or other set time interval). Small gaps (usually less than 3 seconds) in the data are filled using the linear interpolation; if a large gap exists, the data is marked as "missing". All data is then combined into one set, which includes vehicle speed and engine operating parameters, such as intake/fuel/exhaust flow, and exhaust concentrations.

A number of parameters are required to calculate the mass exhaust flow, including composition of air (known), fuel (can be obtained) and exhaust gas (measured by exhaust analyzer 16), the molecular weight of air, fuel and measured pollutants, and the flow (in moles per second) of air or fuel entering the engine, obtained using the above procedure. Flows in grams per second or other units can be converted using simple arithmetic. It is assumed that hydrocarbons can be represented as propane, $C_3H_8$ (any compound can be used, as long as equations are updated accordingly). It is also assumed that fuel can be represented by a hypothetical compound $C_xH_yO_z$. Engine 17 is a closed system, so that balance equations must be satisfied for carbon, hydrogen and oxygen:

$$MF_f(x) = (MF_e)(3c_e(HC) + c_e(CO) + c_e(CO_2)) \quad (1)$$

$$MF_f(y) = 2MF_w + (8c_e(HC)(Mf_e)) \quad (2)$$

$$MF_f(z) + (2MF_i(0.210(21.0\% \text{ oxygen in ambient air})) = MF_w + MF_e(2c_e(O_2) + c_e(CO) + 2c_e(CO_2) + c_e(NO_x)) \quad (3)$$

MF is mass flow [moles/second], c is relative concentration [dimensionless]. The indices are: i=intake; e=exhaust without water; f=fuel; w=water contained in exhaust; HC, CO, $CO_2, O_2, NO_x$=measured pollutants; and C, H, O=atomic carbon, hydrogen, oxygen respectively. This set of three linear equations with three unknowns ($MF_e$, $MF_f$ or $MF_i$, $MF_w$) is then solved for the exhaust mass flow. Calculation from a known fuel flow is similar. Also, if total exhaust flow (dry exhaust plus water) is required, the system can be solved for $MF_w$, and total exhaust flow obtained by adding $MF_w$ and $MF_e$. The set of equations can also be solved for fuel flow, allowing for fuel consumption monitoring. Substituting for $MF_w$ from (2) to (3):

$$MF_f(z-0.5y) + MF_i(2(0.210)) = MF_e(2c_e(O_2) + c_e(CO) + 2c_e(CO_2) + c_e(NO_x) - 4c_e(HC)) \quad (4)$$

Substituting for $MF_f$ from (1) to (4):

$$MF_e(((x)(2c_e(O_2) + c_e(CO) + 2c_e(CO_2) + c_e(NO_x) - 4c_e(HC)) - (3c_e(HC) + c_e(CO) + c_e(CO_2)))(z-0.5y)) = (x)(2)(0.210)(MF_i) \quad (5)$$

Solving for exhaust gas mass flow, yields:

$$MF_e = \frac{(0.420)(x)(MF_i)}{(x(2c_e(O_2) + c_e(CO) + 2c_e(CO_2) + c_e(NO_x) - 4c_e(HC))) - ((3c_e(HC) + c_e(CO) + c_e(CO_2))(z - 0.5y))}$$

Mass emissions for a pollutant X are obtained, for each second, using the following formula:

$$X[\text{grams/second}] = (\text{exhaust flow}[\text{moles/sec}])(\text{concentration}(X))(\text{mol.wt.}(X))$$

Processor 19 is programmed to use this data for several purposes. First, mass emissions in grams/mile for the trip can be calculated by adding all grams/second data for the trip, and dividing by the total distance. The total distance is obtained by adding vehicle speed data in miles per second for the trip, excluding the sections during which there is "missing data". (Miles/second=miles/hour÷3600). If the speed data is not available, the distance can be obtained from the vehicle odometer. Second, real-time mass emissions in grams/mile can be calculated by dividing grams/second emissions by instantaneous vehicle speed in miles/second. Third, fuel consumption, both total and real-time, can be obtained by solving the set of equations for fuel flow in moles/second, and multiplying the results by the fuel molecular weight (for grams/second) and, when needed, by fuel density (for gallons/second data). Fourth, real-time mass emissions in grams/gallon can be obtained by dividing grams/second emissions by fuel flow. Fifth, total mass emissions in gramsgallon can be obtained either by integrating the real-time mass emissions data, or by dividing the total emissions for the trip by the total fuel consumption for the trip.

Modifications

The present invention contemplates that many changes and modifications may be made. The particular materials of which the various body parts and component parts are formed are not deemed critical and may be readily varied.

Therefore, while the presently-preferred form of the emissions measuring system has been shown and described, and several modifications discussed, persons skilled in this art will readily appreciate that various additional changes and modifications may be made without departing from the spirit of the invention, as defined and differentiated by the following claims.

What is claimed is:

1. A portable mass emissions measuring system for an internal combustion engine, comprising:

an exhaust analyzer, a sensor array which may be temporarily attached to said engine for sensing parameters of said engine, said sensor array comprising a first sensor capable of sensing engine rpm, a second sensor capable of sensing a parameter for determining intake air temperature, and a third sensor capable of sensing intake manifold pressure, and a processor programmed to collect and manipulate data from said analyzer and said sensor array, whereby the mass emissions of said engine may be calculated.

2. The emissions measuring system as set forth in claim 1, and further comprising a display for displaying the mass emissions of said engine.

3. The emissions measuring system as set forth in claim 1, wherein said third sensor is capable of sensing the intake charge pressure of said engine.

4. The emissions measuring system as set forth in claim 1, wherein said second sensor is capable of sensing engine oil temperature.

5. The emissions measuring system as set forth in claim 1, wherein said exhaust analyzer measures concentrations of engine exhaust constituents.

6. The emissions measuring system as set forth in claim 1, wherein said exhaust analyzer is capable of determining concentrations of particulate matter in said engine emissions.

7. The emissions measuring system as set forth in claim 1, wherein said exhaust analyzer is capable of determining concentrations of aerosols in said engine emissions.

8. The emissions measuring system as set forth in claim 1, wherein said exhaust analyzer is capable of determining concentration of gases in said engine emissions.

9. The emissions measuring system as set forth in claim 1, wherein said exhaust analyzer, said sensor and said processor are adapted for use on-board a moving vehicle.

10. The emissions measuring system as set forth in claim 1, wherein said second sensor is capable of sensing engine coolant temperature.

11. The emissions measuring system as set forth in claim 1, wherein said second sensor is capable of sensing engine intake air temperature.

12. The emissions measuring system as set forth in claim 1, and further comprising an engine-control interface.

13. The emissions measuring system as set forth in claim 12, wherein said exhaust analyzer, said engine-control interface and said processor are adapted for use on-board a moving vehicle.

14. A method of calculating the mass emissions of an internal combustion engine, comprising the steps of:

providing a sensor array, connecting said sensor array to said engine, providing a gas analyzer, connecting said gas analyzer to the exhaust of said engine providing a processor, programming said processor to:

read data from said sensor array and said gas analyzer determine intake air temperature, determine intake air mass flow, determine exhaust mass flow, determine mass emissions.

15. The method as set forth in claim 14, and further comprising the steps of:

determining the engine oil temperature, determining the ambient air temperature, and wherein said intake air temperature is determined by averaging said engine oil temperature and said ambient air temperature.

16. The method as set forth in claim 14, and further comprising the steps of:

determining engine coolant temperature, determining ambient air temperature, and wherein said intake air temperature is determined by averaging said engine coolant temperature and said ambient air temperature.

17. The method set forth in claim 14, and further comprising the step of calibrating said data based on the predetermined delay time of said sensor array and said gas analyzer.

18. The method set forth in claim 14, wherein said gas analyzer includes an insert probe and said gas analyzer is connected to said exhaust of said engine by inserting said probe in said exhaust of said engine.

19. The method as set forth in claim 14, wherein said processor is programmed to read gas concentration data from said gas analyzer and wherein said exhaust mass flow is determined from said intake air mass flow and said gas concentration data.

20. The method as set forth in claim 19, wherein said mass emissions are determined from said exhaust mass flow and said gas concentration data.

* * * * *